United States Patent [19]

Kamada et al.

[11] Patent Number: 4,997,650

[45] Date of Patent: * Mar. 5, 1991

[54] INSECTICIDAL RESIN COATING FILM

[75] Inventors: Keiichi Kamada; Seiji Kawamoto, both of Chiba; Makoto Yaegashi; Shiro Shiraishi, both of Kanagawa, all of Japan

[73] Assignee: Mitsui Toatsu Chemicals, Inc., Tokyo, Japan

[*] Notice: The portion of the term of this patent subsequent to Apr. 4, 2006 has been disclaimed.

[21] Appl. No.: 260,194

[22] Filed: Nov. 16, 1988

Related U.S. Application Data

[62] Division of Ser. No. 81,471, Aug. 4, 1987, Pat. No. 4,818,525.

[30] Foreign Application Priority Data

| Aug. 8, 1986 | [JP] | Japan | 61-185222 |
| Sep. 1, 1986 | [JP] | Japan | 61-203737 |
| Sep. 2, 1986 | [JP] | Japan | 61-205104 |
| Sep. 2, 1986 | [JP] | Japan | 61-205105 |
| Sep. 3, 1986 | [JP] | Japan | 61-205897 |
| Sep. 12, 1986 | [JP] | Japan | 61-214006 |

[51] Int. Cl.$^5$ ............... A01N 25/08; A01N 25/32; A01N 25/34; A61K 9/58

[52] U.S. Cl. ............... 424/409; 424/78; 424/81; 424/403; 424/405; 424/406; 424/411; 424/487; 424/DIG. 10; 424/DIG. 11; 514/717; 514/718; 514/720; 514/721

[58] Field of Search ............... 424/78, 81, 403, 409, 424/411, 405, 406, 487, DIG. 10, DIG. 11; 514/718, 720, 717, 721

[56] References Cited

U.S. PATENT DOCUMENTS

| 3,228,830 | 1/1966 | McFadden | 424/78 |
| 4,265,876 | 5/1981 | Feakins | 424/28 |
| 4,536,388 | 8/1985 | Pearce, III | 424/411 |
| 4,722,815 | 2/1988 | Subanei | 514/58 |
| 4,818,525 | 4/1989 | Kamada et al. | 424/81 |

FOREIGN PATENT DOCUMENTS 62-212302  9/1987  Japan.

Primary Examiner—Merrell C. Cashion, Jr.
Assistant Examiner—Carlos Azpuru
Attorney, Agent, or Firm—Kane, Dalsimer, Sullivan, Kurucz, Levy, Eisele and Richard

[57] ABSTRACT

An insecticidal resin coating film comprising a combination of an acrylonitrile and/or methacrylonitrile copolymer resin and an insecticidal component selected from the group consisting of specified compounds exhibits an insecticidal effect, since the compound is kept on the surface of the coating film in a state capable of exhibiting its insecticidal effect for a long period of time.

3 Claims, No Drawings

INSECTICIDAL RESIN COATING FILM

This is a divisional of co-pending application Ser. No. 081,471 filed on Aug. 4, 1987, U.S. Pat. No. 4,818,525.

BACKGROUND OF THE INVENTION

1. Field of the Invention

The present invention relates to an insecticidal resin coating film which is formed mainly on a substrate so as to continuously and effectively kill and exterminate insects such as cockroaches, flies and termites which crawl thereon.

2. Prior Art

Compositions comprising an insecticidal component and a high molecular resin used heretofore can be classified into those in the form of an emulsion to be sprayed on the soil to kill insects therein (Japanese Patent Laid-Open No. 58-93738) and those in the form of a sheet or coating film to be used for killing insects in institutions and houses.

The products comprising latter composition include, for example, a paper or fibrous material coated or impregnated with an insecticidal component or insect repellent (Japanese Patent Publication No. 3761/1986), a mixture of latex and an insectproofing agent (Japanese Patent Laid-Open No. 60-238376) and a high molecular resin containing an insecticidal component (GB 2142239 A). However, they are yet insufficient in the application range, insecticidal effect, effect-lasting time and safety. Under these conditions, an improvement of them has been demanded.

SUMMARY OF THE INVENTION

An object of the present invention is to provide an insecticidal resin coating film having a strong, long lasting insecticidal effect, high safety and wide application range.

The inventors have found that the above-mentioned problems can be solved by a coating film comprising a specified resin component containing a specified insecticidal component which film is capable of keeping the effective insecticidal component on the surface of the coating film over a long period of time. The present invention has been completed on the basis of this finding.

The present invention provides an insecticidal resin coating film characterized by comprising 100 parts dry base by weight of a copolymer of acrylonitrile and/or methacrylonitrile and another monomer and 0.1 to 10 parts dry base by weight of an insecticidal component of any of the following general formulae (I) to (XII):

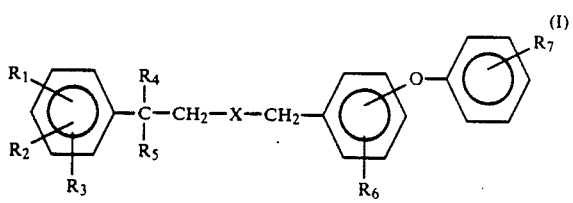

wherein $R_1$, $R_2$ and $R_3$ each represent a hydrogen or halogen atom or a lower alkyl, lower haloalkyl, lower alkoxy, lower haloalkoxy or methylenedioxy group, $R_4$ represents a lower alkyl group, $R_5$ represents a hydrogen atom or a methyl or ethyl group, or $R_4$ and $R_5$ may form a cycloalkyl group having 3 to 6 carbon atoms together with carbon atom bonded with them, the cycloalkyl group being unsubstituted or substituted with a halogen atom or a methyl group, $R_6$ represents a hydrogen or halogen atom, $R_7$ represents a hydrogen or halogen atom or a lower alkyl or lower alkoxy group and X represents an oxygen or sulfur atom or a methylene group;

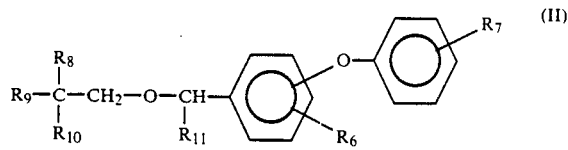

wherein $R_8$, $R_9$ and $R_{10}$ each represent a hydrogen or halogen atom or a lower alkyl group, $R_{11}$ represents a hydrogen atom or a cyano or ethynyl group and $R_6$ and $R_7$ are as defined above;

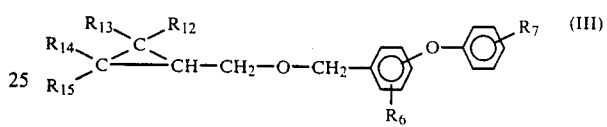

wherein $R_{12}$, $R_{13}$, $R_{14}$ and $R_{15}$ each represent a hydrogen or halogen atom or a lower alkyl or lower alkenyl group, and $R_6$ and $R_7$ are as defined above; ester-type pyrethroid compounds of the general formula:

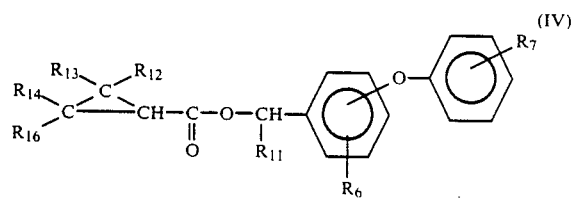

wherein $R_6$, $R_7$, $R_{11}$, $R_{12}$, $R_{13}$ and $R_{14}$ are as defined above and $R_{16}$ represents a hydrogen or halogen atom or a lower alkyl, lower alkenyl or halogen-substituted lower alkenyl group;

ester-type pyrethroid compounds of the general formula:

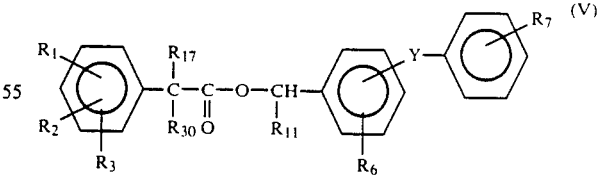

$R_1$, $R_2$, $R_3$, $R_6$, $R_7$ and $R_{11}$ are as defined above, $R_{17}$ represents a lower alkyl group, $R_{30}$ represents a hydrogen atom or $R_{17}$ and $R_{30}$ form an unsubstituted or substituted cycloalkyl group together with the carbon atom bonded with them, and Y represents an oxygen atom, —NH— group or methylene group;

ester-type pyrethroid compounds of the general formula:

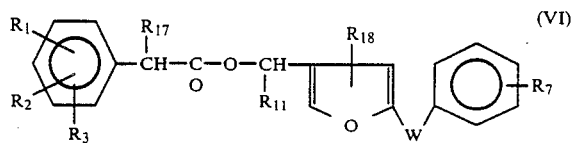

$R_1$, $R_2$, $R_3$, $R_7$, $R_{11}$ and $R_{17}$ are as defined above, $R_{18}$ represents a hydrogen or halogen atom or a lower alkyl or lower alkoxy group and W represents an oxygen atom or a methylene group;

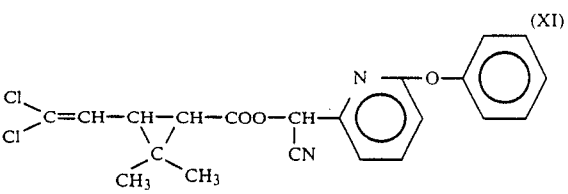

6-phenoxypyridyl-α-cyanomethyl 2,2-dimethyl-3-(4-tertbutylphenyl)cyclopropanecarboxylate:

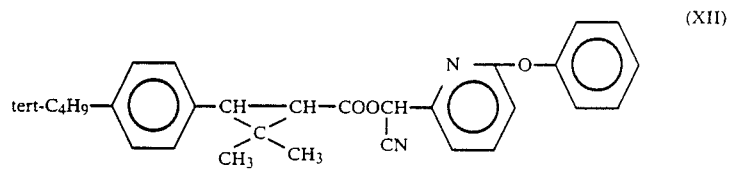

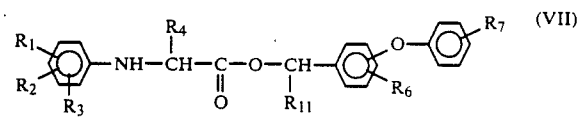

wherein $R_1$, $R_2$, $R_3$, $R_4$, $R_6$, $R_7$ and $R_{11}$ are as defined above;
pentafluorobenzyl 2,2-dimethyl-3-(2,2-dichlorovinyl)-cyclopropanecarboxylate:

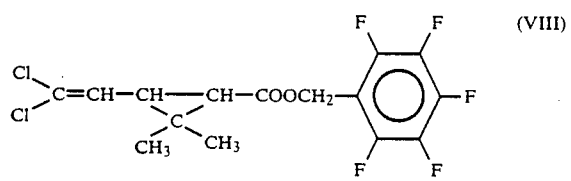

3'-phenylbenzyl 2,2-dimethyl-3-(2,2-dichlorovinyl)cyclopropanecarboxylate:

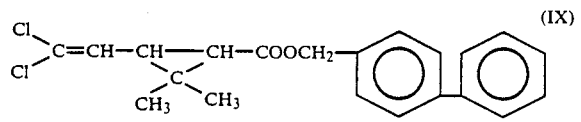

2'-methyl-3'-phenylbenzyl 3-(2-chloro-2-trifluoromethylvinyl)cyclopropanecarboxylate:

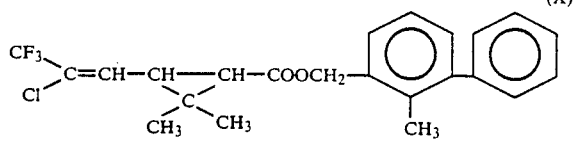

6-phenoxypyridyl-α-cyanomethyl 2,2-dimethyl-3-(2,2-dichlorovinyl)cyclopropanecarboxylate:

DETAILED DESCRIPTION OF THE INVENTION

A resin prepared by copolymerizing (meth)acrylonitirle with another monomer is used as the resin component in the present invention, since the inventors have found that when such a resin is used together with a specified insecticidal component, a coating film capable of exhibiting the remarkable effect of the insecticidal component can be formed. When a given insecticidal component in a given amount is incorporated in various resins and coating films are formed from the resins, coating films prepared from some resins exhibit no insecticidal effect and those prepared from some other resins exhibit only an extremely weak insecticial effect. On the contrary, when the resin of the present invention is used, a coating film exhibiting a surprisingly remarkable insecticidal effect can be prepared. When the special combination of the resin and the insecticidal compound is employed, the compound migrates onto the coating film surface to effectively exhibit its effect over a long period of time.

Examples of the monomers other than (meth)acrylonitrile usable as the comonomer in the present invention include acrylic esters such as methyl, ethyl, isopropyl, n-butyl, isobutyl, n-amyl, isoamyl, n-hexyl, 2-ethylhexyl, n-octyl, decyl and dodecyl acrylates; methacrylic esters such as methyl, ethyl, propyl, n-butyl, isobutyl, n-amyl, isoamyl, n-hexyl, n-octyl, 2-ethylhexyl, decyl and dodecyl methacrylates; styrene monomers such as styrene, vinyltoluene, 2-methylstyrene, t-butylstyrene and chlorostyrene; hydroxyl group-containing monomers such as hydroxyethyl acrylate, hydroxypropyl acrylate, hydroxypropyl methacrylate and hydroxyethyl methacrylate; N-substituted (meth)acrylic monomers such as N-methylol(meth)acrylamide and N-butoxy(meth)acrylamide; and epoxy group-containing monomers such as glycidyl acrylate and glycidyl methacrylate. These monomers can be used either singly or as a combination of them. Among them, the methacrylic esters and styrene are preferred.

The amount of the (meth)acrylonitrile is 5 to 65 wt. %, preferably 15 to 50 wt. %, based on the copolymer resin and the amount of other monomer(s) is 95 to 35 wt. %. When the amount of (meth)acrylonitrile is less than 5 wt. %, the insecticidal effect is not always sufficient and when it exceeds 65 wt. %, the coating film cannot be formed easily.

The copolymer resin of the present invention can be prepared by polymerizing a given amount of the above mentioned (meth)acrylonitrile and other monomer(s) by a known polymerization method such as emulsion polymerization, solution polymerization, suspension polymerization or mass polymerization method.

The molecular weight of the polymer thus prepared is usually 20,000 to 200,000, preferably 50,000 to 150,000.

Examples of the insecticidal components of the present invention include compounds described below.

Examples of the insecticidal components of the present invention represented by the general formula (I):

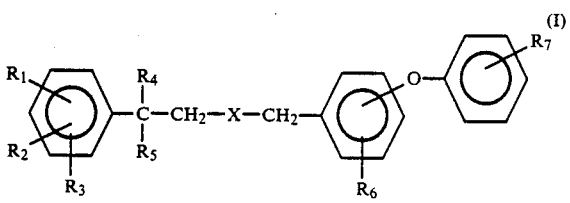

include the following compounds (Ia) to (Id) and, among them, compounds (Ia) to (Ic) exhibit particularly excellent effects:

(Ia): compounds of the general formula (I) wherein X represents an oxygen atom, $R_5$ represents a methyl group, $R_6$ represents a hydrogen atom and $R_7$ represents a hydrogen or halogen atom, (Ib): compounds of the general formula (I) wherein X represents an oxygen or sulfur atom, $R_6$ represents a halogen atom and $R_7$ represents a hydrogen or halogen atom or a lower alkoxy group, (Ic): compounds of the general formula (I) wherein X represents a methylene group, and (Id): compounds of the general formula (I) wherein $R_5$ represents a hydrogen atom and $R_6$ and $R_7$ each represent a hydrogen or halogen atom.

Examples of the above-mentioned compounds include the following ones:

Compounds (Ia)

3-phenoxybenzyl 2-(4-methylphenyl)-2-methylpropyl ether,
3-phenoxybenzyl 2-(4-bromophenyl)-2-ethylpropyl ether,
3-phenoxybenzyl 2-(3-chloro-4-methylphenyl)-2-methylpropyl ether,
3-phenoxybenzyl 2-(3,4-dibromophenyl)-2-methylpropyl ether,
3-phenoxybenzyl 2-(4-chlorophenyl)-2-ethylpropyl ether,
3-phenoxybenzyl 2-(4-tert-butylphenyl)-2-methylpropyl ether,
3-phenoxybenzyl 2-(4-chlorophenyl)-2-methylpropyl ether,
3-phenoxybenzyl 2-(3-bromo-4-chlorophenyl)-2-ethylpropyl ether,
3-phenoxybenzyl 2-(3,4-dichlorophenyl)-2-methylpropyl ether,
3-phenoxybenzyl 2-(4-bromophenyl)-2-methylpropyl ether,
3-phenoxybenzyl 2-(4-ethylphenyl)-2-methylpropyl ether,
3-phenoxybenzyl 2-(4-fluorophenyl)-2-ethylpropyl ether,
3-phenoxybenzyl 2-(3-chloro-4-fluorophenyl)-2-ethylpropy ether,
3-phenoxybenzyl 2-(4-ethylphenyl)-2-ethylpropyl ether,
3-phenoxybenzyl 2-(3,4-dichlorophenyl)-2-ethylpropyl ether,
3-phenoxybenzyl 2-(4-chloro-3-methylphenyl)-2-methylpropyl ether,
3-phenoxybenzyl 2-(4-tert-butylphehyl)-2-ethylpropyl ether,
3-phenoxybenzyl 2-(3,4-dimethylphenyl)-2-methylpropyl ether,
3-phenoxybenzyl 2-(3-chloro-4-methylphenyl)-2-ethylpropyl ether,
3-phenoxybenzyl 2-(3-bromo-4-chlorophenyl)-2-methylpropyl ether,
3-phenoxybenzyl 2-(3,4-dibromophenyl)-2-ethylpropyl ether,
3-phenoxybenzyl 2-(4-chloro-3-methylphenyl)-2-ethylpropyl ether,
3-phenoxybenzyl 2-(4-chlorophenyl)-2-methylpropyl ether,
3-phenoxybenzyl 2-(3,4-dimethylphenyl)-2-ethylpropyl ether,
3-phenoxybenzyl 2-(4-methylphenyl)-2-ethylpropyl ether,
3-phenoxybenzyl 2-(3-chloro-4-fluorophenyl)-2-methylpropyl ether,
3-phenoxybenzyl 2-(3,4-difluorophenyl)-2-methylpropyl ether,
3-phenoxybenzyl 2-(3,4-difluorophenyl)-2-ethylpropyl ether,
3-phenoxybenzyl 2-(3-bromo-4-fluorophenyl)-2-methylpropyl ether,
3-phenoxybenzyl 2-(3-bromo-4-fluorophenyl)-2-ethylpropyl ether,
3-phenoxybenzyl 2-(3-fluoro-4-bromophenyl)-2-methylpropyl ether,
3-phenoxybenzyl 2-(4-methoxyphenyl)-2-methylpropyl ether,
3-phenoxybenzyl 2-(4-methoxyphenyl)-2-ethylpropyl ether,
3-phenoxybenzyl 2-(4-ethoxyphenyl)-2-methylpropyl ether,
3-phenoxybenzyl 2-(4-ethoxyphenyl)-2-ethylpropyl ether,
3-phenoxybenzyl 2-(4-propoxyphenyl)-2-methylpropyl ether,
3-phenoxybenzyl 2-(4-propoxyphenyl)-2-ethylpropyl ether,
3-phenoxybenzyl 2-(4-pentyloxyphenyl)-2-methylpropyl ether,
3-phenoxybenzyl 2-(3-chloro-4-ethoxyphenyl)-2-methylpropyl ether,
3-phenoxybenzyl 2-(3-bromo-4-ethoxyphenyl)-2-methylpropyl ether,
3-phenoxybenzyl 2-(4-difluoromethoxyphenyl)-2-methylpropyl ether,
3-phenoxybenzyl 2-(4-difluoromethoxyphenyl)-2-ethylpropyl ether,
3-phenoxybenzyl 2-(4-trifluoromethoxyphenyl)-2-methylpropyl ether,
3-phenoxybenzyl 2-(4-chlorodifluoromethoxyhenyl)-2-methylpropyl ether,
3-phenoxybenzyl 2-(4-bromodifluoromethoxyphenyl)-2-methylpropyl ether, 3-phenoxybenzyl 2-(3,4-methylenedioxyphenyl)-2-methylpropyl ether, and 3-phenoxybenzyl 2-(4-trifluoromethylphenyl)-2-methylpropyl ether.

Compounds (Ib)

3-(4-fluorophenoxy)-4-fluorobenzyl 2-(4-chlorophenyl)-2-methylpropyl ether, 3-phenoxy-4-fluorobenzyl 2-(phenyl-2-methylpropyl ether, 3-phenoxy-4-chlorobenzyl 2-(4-chlorophenyl)-2-methylpropyl ether, 3-phenoxy-4-fluorobenzyl 2-(4-methoxyphenyl)-2-methylpropyl ether, 3-phenoxy-4-fluorobenzyl 2-(3,4-dimethylphenyl)-2-methylpropyl ether, 3-(4-fluorophenoxy)-4-fluorobenzyl 2-(4-methoxyphenyl)-2-methylpropyl ether, 3-phenoxy-4-fluorobenzyl 2-(4-chlorophenyl)-2-ethylbutyl ether, 3-phenoxy-4-fluorobenzyl 2-(4-chlorophenyl)butyl ether, 3-phenoxy-6-chlorobenzyl 2-(4-chlorophenyl)-2-methylpropyl ether, 3-phenoxy-4-fluorobenzyl 2-(4-chlorophenyl)-3-methylbutyl ether, 3-(4-fluorophenoxy)-4-fluorobenzyl 2-(3,4-dichlorophenyl)-2-methylbutyl ether, 3-phenoxy-4-fluorobenzyl 2-(4-ethoxyphenyl)-2-methylpropyl ether, 3-(3-chlorophenoxy)-4-fluorobenzyl 2-(4-chlorophenyl)-2-methylpropyl ether, 3-(3-chlorophenoxy)-4-fluorobenzyl 2-(3,4-dimethyl)-2,3-dimethylbutyl ether, 3-phenoxy-4-fluorobenzyl 2-(4-chlorophenyl)-2-methylpropyl ether, 3-(2-fluorophenoxy)-4-fluorobenzyl 2-(3-chloro-4-chlorophenoxy)-2-methylpropyl ether, 3-(2-fluorophenoxy)-4-fluorobenzyl 2-(4-chlorophenyl)-2-methylpropyl ether, 3-(4-fluorophenoxy)-4-chlorobenzyl 2-(3,4-dimethoxyphenyl)-2-butylpropyl ether, 3-phenoxy-4-fluorobenzyl 2-(4-methoxy-3,5-dimethylphenyl)-2-methylpropyl ether, 3-phenoxy-4-fluorobenzyl 2-(4-tert-butylphenyl)-2-methylpropyl ether, 3-(4-methoxyphenoxy)-4-fluorobenzyl 2-(4-chlorophenyl)-2-methylpropyl ether, 3-phenoxy-4-fluorobenzyl 2-(3,4-dichlorophenyl)-2-methylpropyl ether, 3-(4-bromophenoxy)-4-fluorobenzyl 2-(4-chlorophenyl)-2-methylpropyl ether, 3-(4-fluorophenoxy)-4-fluorobenzyl 2-(4-ethoxyphenyl)-2-methylpropyl ether, 3-(4-ethoxyphenyl)-4-fluorobenzyl 2-(4-ethoxyphenyl)-2-methylpropyl ether, 3-phenoxy-4-fluorobenzyl 2-(4-difluoromethoxyphenyl)-2-methylpropyl ether, 3-(4-fluorophenoxy)-4-fluorobenzyl 2-(4-difluoromethoxyphenyl)-2-methylpropyl ether, 3-phenoxy-4-fluorobenzyl 2-(4-trifluoromethoxyphenyl)-2-methylpropyl ether, 3-(4-fluorophenoxy)-4-fluorobenzyl 2-(4-trifluoromethoxyphenyl)-2-methylpropyl ether, 3-phenoxy-4-fluorobenzyl 2-(4-chlorodifluoromethoxyphenyl)-2-methylpropyl ether, 3-(4-fluorophenoxy)-4-fluorobenzyl 2-(4-chlorodifluoromethoxyphenyl)-2-methylpropyl ether, 3-phenoxy-4-fluorobenzyl 2-(4-bromodifluoromethoxyphenyl)-2-methylpropyl ether, 3-(4-fluorophenoxy)-4-fluorobenzyl 2-(4-bromodifluoromethoxyphenyl)-2-methylpropyl ether, 3-phenoxy-4-fluorobenzyl 2-(3,4-methylenedioxyphenyl)-2-methylpropyl ether, 3-(4-fluorophenoxy)-4-fluorobenzyl 2-(3,4-methylenedioxyphenyl)-2-methylpropyl ether, 3-phenoxy-4-fluorobenzyl 2-(4-trifluoromethylphenyl)-2-methylpropyl ether, 3-(4-fluorophenoxy)-4-fluorobenzyl 2-(4-trifluoromethylphenyl)-2-methylpropyl ether, 3-phenoxy-4-fluorobenzyl 2-(4-propoxyphenyl)-2-methylpropyl ether, 3-(4-fluorophenoxy)-4-fluorobenzyl 2-(4-propoxyphenyl)-2-methylpropyl ether, and thioethers corresponding to these ethers.

Compounds (Ic)

1-(3-phenoxyphenyl)-4-(4-methoxyphenyl)-4-methylpentane,

1-{3-(4-fluorophenoxy)phenyl}-4-(4-fluorophenyl)-4-methylhexane, 1-(3-phenoxyphenyl)-4-(4-methoxyphenyl)-4-methylhexane, 1-{3-(4-fluorophenoxy)phenyl}-4-(4-fluorophenyl)-4-methylpentane, 1-{3-(4-fluorophenoxy)phenyl}-4-(4-methylphenyl)-4-methylpentane, 1-{3-(4-bromophenoxy)phenyl}-4-(4-chlorophenyl)-4-methylpentane, 1-{3-(4-bromophenoxy)phenyl}-4-(4-chlorophenyl)-4-methylhexane, 1-(3-phenoxyphenyl)-4-phenyl-4-methylpentane, 1-(3-phenoxyphenyl)-4-phenyl-4-methylhexane, 1-(3-phenoxyphenyl)-4-(4-chlorophenyl)-4-methylhexane, 1-{3-(4-fluorophenoxy)phenyl}-4-(4-chlorophenyl)-4-methylpentane, 1-{3-(4-fluorophenoxy)phenyl}-4-(4-ethoxyphenyl)-4-methylpentane, 1-{3-(4-fluorophenoxy)phenyl}-4-(4-chlorophenyl)-4-methylhexane, 1-{3-(4-fluorophenoxy)phenyl}-4-(3,4-dimethylphenyl)-4-methylpentane, 1-(3-phenoxyphenyl)-4-(3,4-dimethylphenyl)-4-methylpentane, 1-(3-phenoxyphenyl)-4-(3,4-methylenedioxyphenyl)-4-methylpentane, 1-{3-(4-methoxyphenoxy)phenyl}-4-(4-ethoxyphenyl)-4-methylpentane, 1-{3-(3-chlorophenoxy)phenyl}-4-(4-chlorophenyl)-4-methylpentane, 1-{3-(3-chlorophenoxy)phenyl}-4-(4-chlorophenyl)-4-methylhexane, 1-{3-(3-fluorophenoxy)phenyl}-4-(4-chlorophenyl)-4-methylpentane, 1-{3-(3-fluorophenoxy)phenyl}-4-(4-chlorophenyl)-4-methylhexane, 1-{3-(4-fluorophenoxy)phenyl}-4-(4-difluoromethoxyphenyl)-4-methylpentane, 1-{3-(4-fluorophenoxy)phenyl}-4-(4-difluoromethoxyphenyl)-4-methylhexane, 1-{3-(4-methoxyphenoxy)phenyl}-4-phenyl-4-methylpentane, 1-{3-(4-methoxyphenoxy)phenyl}-4-phenyl-4-methylhexane, 1-(3-phenoxyphenyl)-4-(4-ethoxyphenyl)-4-methylpentane,
1-{3-(4-fluorophenoxy)phenyl}-4-(4-ethoxyphenyl)-4-methylpentane,
1-(3-phenoxy-4-fluorophenyl)-4-(4-ethoxyphenyl)-4-methylpentane,
1-{3-(4-fluorophenoxy)-4-fluorophenyl}-4-(4-ethoxyphenyl)-4-methylpentane,
1-{3-(4-ethoxyphenoxy)-4-fluorophenyl}-4-(4-ethoxyphenyl)-4-methylpentane,
1-(3-phenoxy-4-fluorophenyl)-4-(4-chlorophenyl)-4-methylpentane,
1-{3-(4-fluorophenoxy)-4-fluorophenyl}-4-(4-chlorophenyl)-4-methylpentane,
1-{3-phenoxy-4-fluorophenyl)-4-(4-ethoxyphenyl)-4-methylhexane,
1-(3-phenoxyphenyl)-4-(4-difluoromethoxyphenyl)-4-methylpentane,
1-(3-phenoxy-4-fluorophenyl)-4-(4-difluoromethoxyphenyl)-4-methylpentane,
1-{3-(4-fluorophenoxy)-4-fluorophenyl}-4-(4-difluoromethoxyphenyl)-4-methylpentane,
1-(3-phenoxyphenyl)-4-(4-trifluoromethoxyphenyl)-4-methylpentane,
1-(3-phenoxy-4-fluorophenyl)-4-(4-trifluoromethoxyphenyl)-4-methylpentane,
1-{3-(4-fluorophenoxy)phenyl}-4-(4-trifluoromethoxyphenyl)-4-methylpentane,
1-{3-(4-fluorophenoxy)-4-fluorophenyl}-4-(4-trifluoromethoxyphenyl)-4-methylpentane,
1-(3-phenoxyphenyl)-4-(4-chlorodifluoromethoxyphenyl)-4-methylpentane,
1-{3-(4-fluorophenoxy)phenyl}-4-(4-chlorodifluoromethoxyphenyl)-4-methylpentane,
1-(3-phenoxy-4-fluorophenyl)-4-(4-chlorodifluoromethoxyphenyl)-4-methylpentane,
1-{3-(4-fluorophenoxy)-4-fluorophenyl}-4-(4-chlorodifluoromethoxyphenyl)-4-methylpentane,
1-(3-phenoxyphenyl)-4-(4-bromodifluoromethoxyphenyl)-4-methylpentane,
1-{3-(4-fluorophenoxy)phenyl}-4-(4-bromodifluoromethoxyphenyl)-4-methylpentane,
1-(3-phenoxy-4-fluorophenyl)-4-(4-bromodifluoromethoxyphenyl)-4-methylpentane,
1-{3-(4-fluorophenoxy)-4-fluorophenyl}-4-(4-bromodifluoromethoxyphenyl)-4-methylpentane,
1-(3-phenoxyphenyl)-3-{1-(4-ethoxyphenyl)dichloropropyl}-propane,
1-(3-phenoxy-4-fluorophenyl)-3-{1-(4-ethoxyphenyl)-4-cyclopropyl}propane,
1-{3-(4-fluorophenoxy)-4-fluorophenyl}-3-{1-(4-ethoxyphenyl) cyclopropyl}propane,
1-(3-phenoxyphenyl)-3-{4-(4-chlorophenyl)-2,2-dichlorocyclopropyl}propane,
1-(3-phenoxy-4-fluorophenyl)-3-{1-(4-chlorophenyl)-2,2-dichlorocyclopropyl}propane,
1-{3-(4-fluorophenoxy)-4-fluorophenyl}-3-{1-(4-chlorophenyl)-2,2-dichlorocyclopropyl}propane,
1-(3-phenoxyphenyl)-3-{1-(4-ethoxyphenyl)-2,2-difluorocyclopropyl}propane,
1-(3-phenoxy-4-fluorophenyl)-3-{1-(4-ethoxyphenyl)-2,2-difluorocyclopropyl}propane,
1-{3-(4-fluorophenoxy)phenyl}-3-{1-(4-ethoxyphenyl)-2,2-difluorocyclopropyl}propane,
1-{3-(4-fluorophenoxy)-4-fluorophenyl}-3-{1-(4-ethoxyphenyl)-2,2-difluorocyclopropyl}propane,
1-(3-phenoxyphenyl)-3-{1-(4-ethoxyphenyl)-cyclobutyl}propane,
1-(3-phenoxy-4-fluorophenyl)-3-{1-(4-ethoxyphenyl)-cyclobutyl}propane,
1-(3-phenoxyphenyl)-3-{1-(4-ethoxyphenyl)-3,3-dichlorocyclobutyl}propane,
1-(3-phenoxy-4-fluorophenyl)-3-{1-(4-ethoxyphenyl)-3,3-dichlorocyclobutyl}propane,
1-(3-phenoxyphenyl)-3-{1-(4-ethoxyphenyl)-2,2-dimethylcyclopropyl}propane, and
1-(3-phenoxy-4-fluorophenyl)-3-{1-(4-ethoxyphenyl)-2,2-dimethylcyclopropyl}propane.

Compounds (Id)

3-phenoxybenzyl 2-(4-chlorophenyl)-2-isopropylethyl ether,
3-phenoxybenzyl 2-(4-methylphenyl)-2-isopropylethyl ether,
3-phenoxybenzyl 2-(4-methoxyphenyl)-2-isopropylethyl ether,
3-phenoxybenzyl 2-(4-chlorophenyl)-2-isopropyl ether sulfide,
3-phenoxybenzyl 2-(3-methylphenyl)-2-isopropylethyl ether,
3-phenoxybenzyl 2-(3,4-dimethoxyphenyl)-2-isopropylethyl ether,
3-phenoxybenzyl 2-(4-ethoxyphenyl)-2-isopropylethyl ether,
3-(4-fluorophenoxy)-4-fluorobenzyl 2-(4-methoxyphenyl)-2-isopropyl ether,
3-(4-fluorophenoxybenzyl) 2-(4-difluoromethoxyphenyl)-2-isopropylethyl ether,
3-phenoxy-4-fluorobenzyl 2-(4-chlorophenyl)-2-isopropylethyl ether, and
3-phenoxy-4-fluorobenzyl-2-(4-ethoxyphenyl)-2-isopropylethyl ether.

Among the insecticidal compounds of the present invention represented by the following general formula (II):

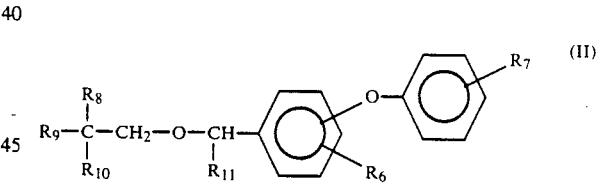

wherein $R_8$, $R_9$ and $R_{10}$ each represent a hydrogen or halogen atom or a lower alkyl group, $R_{11}$ represents a hydrogen atom or a cyano or ethynyl group, and $R_6$ and $R_7$ are as defined above, those having particularly excellent effects include the following compounds:

3-phenoxybenzyl neopentyl ether,
3-phenoxybenzyl 1,1,1-trichloroethyl ether,
α-cyano-3-phenoxybenzyl neopentyl ether,
3-(4-fluorophenoxy)benzyl neopentyl ether,
3-(4-methoxyphenoxy)benzyl neopentyl ether,
3-phenoxybenzyl 2-methylpropyl ether,
α-ethynyl-3-phenoxybenzyl neopentyl ether,
3-phenoxy-4-fluorobenzyl neopentyl ether,
3-(4-fluorophenoxy)-4-fluorobenzyl neopentyl ether, and
α-cyano-3-phenoxy-4-fluorobenzyl neopentyl ether.

Among the insecticidal compounds of the present invention represented by the following general formula (III):

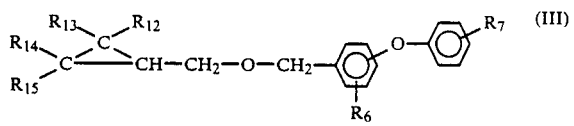

wherein $R_{12}$, $R_{13}$, $R_{14}$ and $R_{15}$ each represent a hydrogen or halogen atom or a lower alkyl or lower alkenyl group, and $R_6$ and $R_7$ are as defined above, those having particularly excellent effects include the following compounds:

3-phenoxybenzyl 2,2,3,3-tetramethylcyclopropylmethyl ether,
3-phenoxybenzyl 2,2-dimethyl-3-isobutenylcyclopropylmethyl ether,
3-phenoxybenzyl 2,2-dimethylcyclopropylmethyl ether,
3-phenoxybenzyl cyclopropylmethyl ether,
3-(4-chlorophenoxy)benzyl 2,2-dichlorocyclopropylmethyl ether, and
3-phenoxy-4-fluorobenzyl cyclopropylmethyl ether.

Examples of the insecticidal ester-type pyrethroid compounds of the present invention represented by the following general formula (IV):

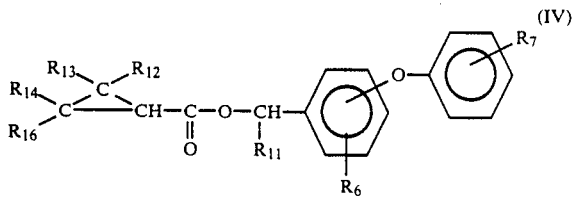

wherein $R_6$, $R_7$, $R_{11}$, $R_{12}$, $R_{13}$ and $R_{14}$ are as defined above and $R_{16}$ represents a hydrogen or halogen atom or a lower alkyl, lower alkenyl or halogen-substituted lower alkenyl group,
include the following compounds:

3'-phenoxybenzyl 2,2-dimethyl-3-isobutenylcyclopropanecarboxylate,
3'-phenoxybenzyl 2,2-dimethyl-3-(2,2-dichlorovinyl)cyclopropanecarboxylate,
3'-phenoxy-α-cyanobenzyl 2,2-dimethyl-3-isobutenylcyclopropanecarboxylate,
3'-phenoxy-α-cyanobenzyl 2,2-dimethyl-3,3-dimethylcyclopropanecarboxylate,
3'-phenoxy-4'-fluorobenzyl 2,2,3,3-tetramethylcyclopropanecarboxylate,
3'-phenoxy-α-cyanobenzyl 2,2,3,3-tetramethylcyclopropanecarboxylate,
3'-phenoxy-4'-fluorobenzyl-2,2-dimethyl-3-(2,2-dichlorovinyl)cyclopropanecarboxylate,
3'-phenoxy-α-cyano-4'-fluorobenzyl 2,2-dimethyl-3-(2,2-dichlorovinyl)cyclopropanecarboxylate,
3'-phenoxybenzyl 2,2-dimethyl-3-(2-chloro-2-trifluoromethylvinyl)cyclopropanecarboxylate,
3'-phenoxy-α-cyano-4'-fluorobenzyl 2,2-dimethyl-3-(2-chloro-2-trifluoromethylvinyl)cyclopropanecarboxylate,
3'-phenoxy-α-cyanobenzyl 3-(2-chloro-2-trifluoromethylvinyl)cyclopropanecarboxylate,
3'-phenoxy-4'-fluorobenzyl 2,2-dimethyl-3-(2-chloro-2-trifluoromethylvinyl)cyclopropanecarboxylate,
3'-phenoxybenzyl 2,2-dimethyl-3-(2,2-dibromovinyl)cyclopropanecarboxylate,
3'-phenoxy-α-cyanobenzyl 2,2-dimethyl-3-(2,2-dibromovinyl)cyclopropanecarboxylate,
3'-phenoxy-4'-fluorobenzyl 2,2-dimethyl-3-(2,2-dibromovinyl)cyclopropanecarboxylate,
3'-phenoxy-α-cyano-4'-fluorobenzyl 2,2-dimethyl-3-(2,2-dibromovinyl)cyclopropanecarboxylate,
3'-phenoxy-α-cyanobenzyl 2,2-dimethyl-3-(1,2,2,2-tetrabromoethyl)cyclopropanecarboxylate,
3'-phenoxy-α-cyanobenzyl 2,2-dimethyl-3-(2,2-dibromo-1,2-dichloroethyl)cyclopropanecarboxylate, and
3'-phenoxy-α-cyanobenzyl 2,2-dimethyl-3-(4-tert-butylphenyl)cyclopropanecarboxylate.

Examples of the insecticidal ester-type pyrethroid compounds of the present invention represented by the following general formula (V):

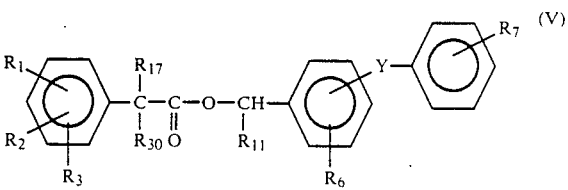

wherein $R_1$, $R_2$, $R_3$, $R_6$, $R_7$ and $R_{11}$ are as defined above, $R_{17}$ represents a lower alkyl group, $R_{30}$ represents a hydrogen atom or $R_{17}$ and $R_{30}$ form an unsubstituted or substituted cycloalkyl group together with the carbon atom bonded with them, and Y represents an oxygen atom, —NH— group or methylene group
include the following compounds:

3'-phenoxybenzyl α-isopropyl(3,4-dimethoxyphenyl)acetate,
3'-phenoxy-α'-cyanobenzyl α-isopropyl(p-ethoxyphenyl)-acetate,
3'-benzylbenzyl α-isopropyl-(3-methoxy-4-methyl)phenylacetate,
3'-phenoxybenzyl α-isopropyl-p-methoxyphenylacetate,
3'-phenoxybenzyl α-ethyl(2,4,6-trimethyl)phenylacetate,
3'-phenoxybenzyl α-ethyl-p-methoxyphenylacetate,
3'-phenoxybenzyl α-isopropenyl-p-methoxyphenylacetate,
3'-benzylbenzyl α-isopropyl-p-methoxyphenylacetate,
3'-phenoxybenzyl α-isopropyl-p-methylthiophenylacetate,
3'-phenoxybenzyl α-isopropenyl-m-methoxyphenylacetate,
3'-phenoxybenzyl α-isopropenyl-3,4-dimethoxyphenylacetate,
3'-phenoxybenzyl α-isopropyl-4-chlorophenylacetate,
3'-phenoxy-α'-cyanobenzyl α-isopropyl-4-chlorophenylacetate,
3'-phenoxy-4'-fluorobenzyl α-isopropyl-4-chlorophenylacetate,
3'-phenoxy-α'-cyano-4'-fluorobenzyl α-isopropyl-4-chlorophenylacetate,
3'-phenoxybenzyl α-isopropyl-4-difluoromethoxyphenylacetate,
3'-phenoxy-α'-cyanobenzyl α-isopropyl-4-difluoromethoxyphenylacetate,
3'-phenoxy-4'-fluorobenzyl α-isopropyl-4-difluoromethoxyphenylacetate,
3'-phenoxy-α'-cyano-4'-fluorobenzyl α-isopropyl-4-difluoromethoxyphenylacetate, 3'-phenoxy-α'-cyanobenzyl 2,2-dichloro-1-(4-ethoxyphenyl)-cyclopropanecarboxylate, and 3'-phenoxy-α'-ethynylbenzyl 1-(4-ethoxyphenyl)-2,2,3,3-tetrafluorocyclobutanecarboxylate.

Examples of the insecticidal ester-type pyrethroid compounds of the present invention represented by the following general formula (VI):

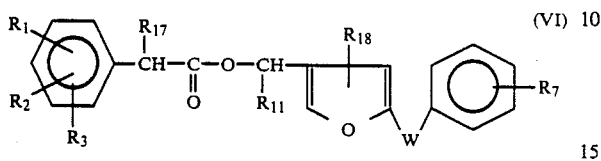

wherein R₁, R₂, R₃, R₇, R₁₁ and R₁₇ are as defined above, R₁₈ represents a hydrogen or halogen atom or a lower alkyl or lower alkoxy group and W represents an oxygen atom or a methylene group include the following compounds:

5'-benzyl-3'-furylmethyl α-isopropyl(p-methoxyphenyl)-acetate,

5'-benzyl-3'-furylmethyl α-ethyl-(m-methoxyphenyl)acetate,

5'-benzyl-3'-furylmethyl α-isopropyl(p-allylphenyl)acetate,

5'-phenoxy-2'-furylmethyl α-isopropyl(2-methyl-4-methoxy)-phenylacetate,

5'-benzyl-3'-furylmethyl α-ethyl-m-methylphenylacetate,

5'-benzyl-3'-thienyl α-isopropyl-2-methyl-3-isopropenylphenylacetate,

5'-benzyl-3'-furylmethyl α-isopropyl-4,5-dimethylphenylacetate,

5'-benzyl-3'-furylmethyl α-isopropyl-3,4-dimethoxyphenylacetate, and

5'-benzyl-3'-furylmethyl α-isopropyl-m-methoxyphenylacetate.

Examples of the insecticidal compounds of the present invention represented by the following general formula (VII):

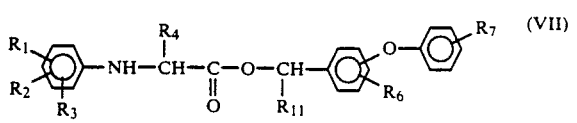

wherein R₁, R₂, R₃, R₄, R₆, R₇ and R₁₁ are as defined above,
include the following compounds:

3'-phenoxybenzyl α-isopropylanilinoacetate,

3'-phenoxybenzyl α-isopropyl-(4-chloroanilino)acetate,

3'-phenoxybenzyl α-isopropyl-(4-methylanilino)acetate,

3'-phenoxy-α'-cyanobenzyl e-isopropyl-(2-chloro-4-trifluoromethylanilino)acetate, 3'-phenoxybenzyl α-isopropyl-(4-trifluoromethylanilino)acetate, and 3'-phenoxy-α'-cyanobenzyl α-isopropyl-4-trifluoromethylanilino)acetate.

Among the insecticidal compounds of the above general formula (I), those of the following general formula (XIV) have particularly excellent effects. Examples of them include those shown in the following Table 1:

TABLE 1

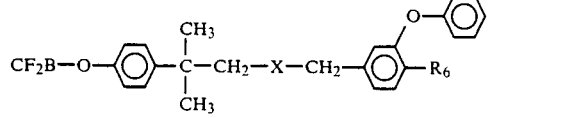

| Compound No. | X | B | R₆ | Refractive index (20° C.) |
|---|---|---|---|---|
| 1 | O | Br | H | 1.5545 |
| 2 | O | Br | F | 1.5440 |
| 3 | CH₂ | Br | H | 1.5482 |
| 4 | CH₂ | Br | F | 1.5480 |
| 5 | O | Cl | H | 1.5441 |
| 6 | O | Cl | F | |
| 7 | CH₂ | Cl | H | |
| 8 | CH₂ | Cl | F | |
| 9 | O | F | H | 1.5312 |
| 10 | O | F | F | 1.5208 |
| 11 | CH₂ | F | H | 1.5340 |
| 12 | CH₂ | F | F | 1.5248 |

Among the compounds of the general formula (XIV), those wherein X represents an oxygen atom [i.e. compounds of the following general formulae (XIVa), (XIVb) and (XIVc)] can be easily prepared from compounds (XV) by the following processes:

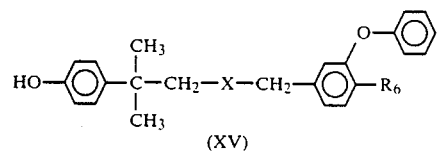

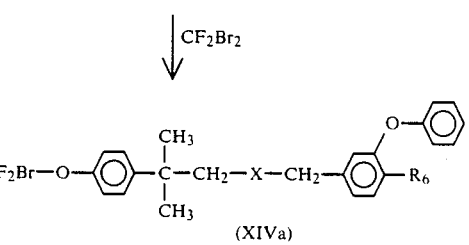

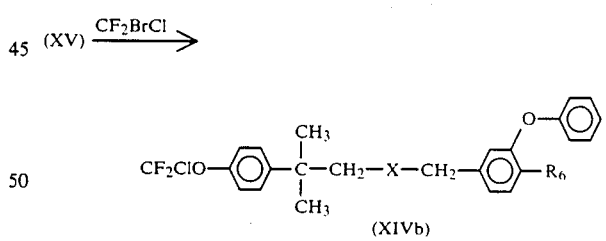

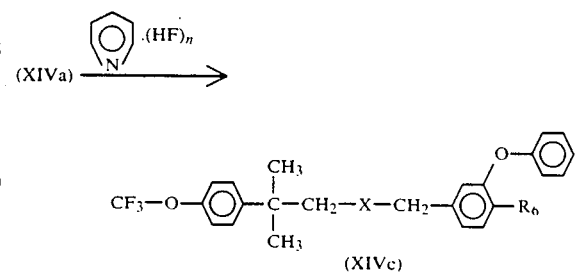

wherein Y is as defined above.

A phenol derivative of the general formula (XV) is reacted with dibromodifluoromethane or difluorobromochloromethane in the presence of a base such as sodium hydride or potassium t-butoxide in a polar solvent such as dimethylformamide (DMF) or 1,3-dimethyl-2-imidazolidinone (DMI) to prepare a compound (XIVa) or (XIVb) (reference: Tetrahedron Letters, 1981, 323). The compound (XIVa) thus prepared is reacted with hydrogen fluoride to prepare a compound (XIVc) (reference: Japanese Patent Laid-Open No. 128374/1983).

Compounds (XIVa), (XIVb) and (XIVc) can be easily prepared from compounds (XVIa), (XVIb) and (XVIc), respectively with compound XVIII by the following processes:

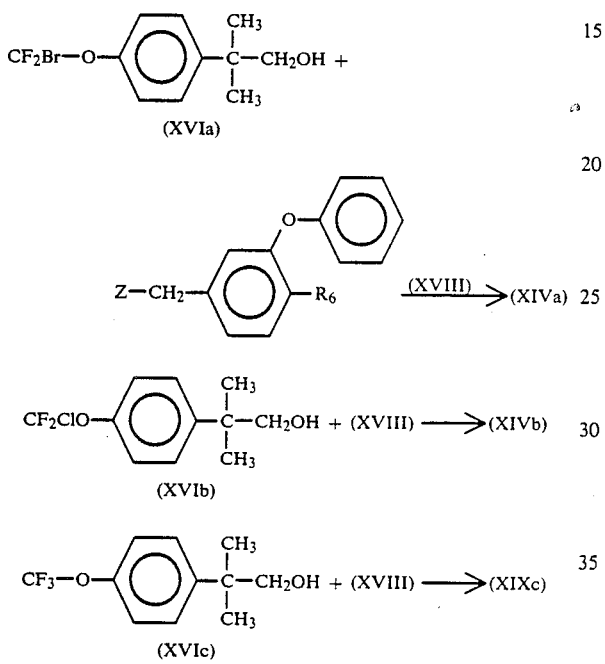

wherein $R_6$ is as defined above and Z represents a halogen atom.

Namely, the intended compounds can be prepared from the 2-aryl-2-methylpropyl alcohols of the above formula (XVIa), (XVIb) or (XVIc) and benzyl halides of the general formula (XVIII) by an ordinary etherification reaction. The 2-aryl-2-methylpropyl alcohols of the formulae (XVIa), (XVIb) and (XVIc) have not been described in literatures. The 2-aryl-2-methylpropyl alcohols of the general formula (XVI) [i.e. general formulae (XVIa), (XVIb) and (XVIc)] can be prepared by the following processes:

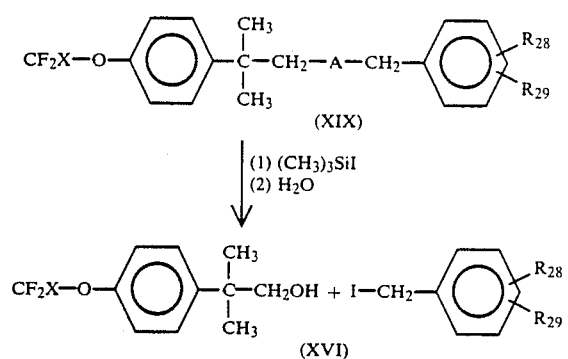

wherein $R_{28}$ and $R_{29}$ each represent a hydrogen or halogen atom or an alkyl, alkoxy or phenoxy group.

In this process, a benzyl ether derivative of the general formula (XIX) is reacted with trimethylsilyl iodide in an inert solvent such as hexane or chloroform and then the product thus obtained is reacted with water to obtain the intended product easily.

The compounds of the general formula (XIV) wherein A represents a methylene group [compounds of the general formulae (XIVd), (XIVe) and (XIVf)] can be prepared easily from compounds of the following formula (XX) as follows:

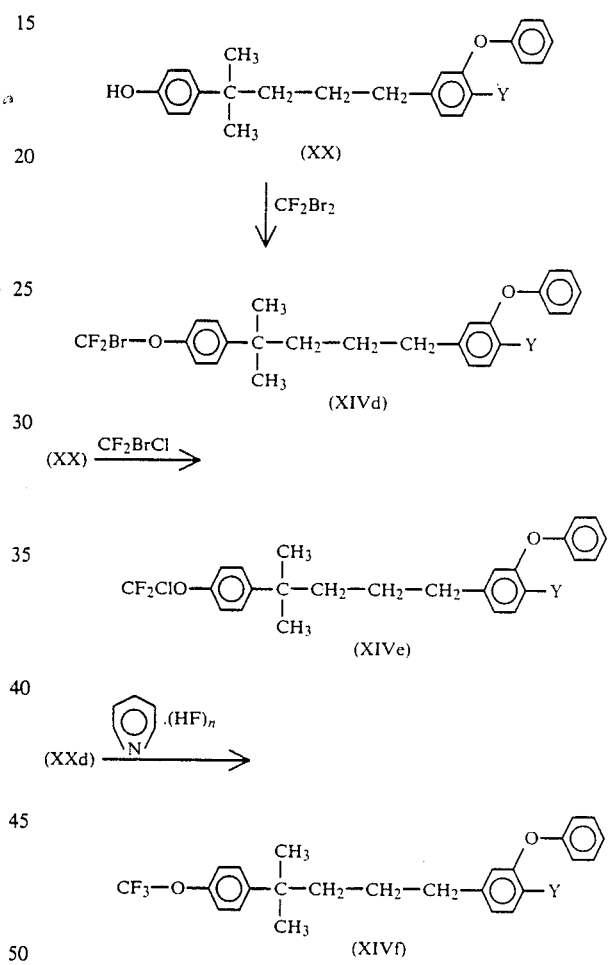

wherein Y is as defined above.

The compounds (XIVd), (XIVe) and (XIVf) can be prepared from the compounds (XV) under the same conditions as in the preparation of the compounds (XIVa), (XIVb) and (XIVc).

The amount of the insecticide is 0.1 to 10 parts by weight, preferably 0.5 to 10 parts by weight, per part of the resin component. When the amount is less than 0.1 part by weight, the insecticidal effect is insufficient and, on the contrary, even when it exceeds 10 parts by weight, the insecticidal effect is no more improved and such an excess amount is economically disadvantageous. The insecticidal resin coating film of the present invention may contain additives in addition to the insecticidal component. The additives include, for example, waxes, fusing agents and plasticizers. Usually excellent effects are obtained when a wax such as carnauba wax, rice bran wax, bees wax, spermaceti, candelilla wax, haze wax, montan wax, ceresine wax, paraffin wax, microcrystalline wax, polyethylene wax or Fischer-Tropsch wax is used.

The insecticidal resin coating film of the present invention can be prepared by, for example, the following processes:

(1) a process wherein an insecticidal component per se or its solution is mixed with an emulsion of a copolymer resin of (meth)acrylonitrile and another monomer, the mixture is applied to a substrate by a known method such as bar coating, roll coating, air knife coating, spray coating, dipping, brush coating or screen printing method and the coating film thus formed is dried, (2) a process wherein (meth)acrylonitrile is emulsion-polymerized with another monomer in the presence of an insecticidal component, the polymer emulsion thus prepared is applied to a substrate by a known method and the coating film thus formed is dried, (3) a process wherein an insecticidal component per se or its solution is mixed with a solution of a copolymer resin of (meth)acrylonitrile and another monomer, the mixture is applied to a substrate by a known method and the coating film thus formed is dried, (4) a process wherein (meth)acrylonitrile is solution-polymerized with another monomer in the presence of an insecticidal component, the polymer solution thus obtained is applied to a substrate by a known method and the coating film thus formed is dried, and (5) a process wherein a copolymer resin of (meth)acrylonitrile and another monomer is kneaded with an insecticidal component by means of a blender such as roll blender and the mixture thus obtained is pressed onto a substrate under heating.

Further, modifications of these processes can also be employed. As a matter of course, the processes are not limited to those mentioned above. Though the drying conditions are not particularly limited in the above processes (1) to (4), the drying is usually conducted at ambient temperature to 150° C. for 1 min to 24 h.

Among the above-mentioned processes, the process (1) is most preferred from the viewpoint of the insecticidal effect.

In case the insecticidal component is used in the form of its solution, the solvents usable therefor include ketones, esters, halogenated hydrocarbons, aromatic hydrocarbons and alicyclic hydrocarbons. These solvents are used either singly or in the form of a mixture of them. The substrates to which the resin is to be applied are not particularly limited. They are preferably papers, synthetic papers, plastic sheets, steel plates, etc. Although the thickness of the coating film is not particularly limited, it is usually 20 to 100 μ.

The following referential examples, preparation examples and examples of the present invention will further illustrate the invention.

REFERENTIAL EXAMPLE 1

Preparation of 3-Phenoxybenzyl 2-(4-Hydroxyphenyl)-2-Methylpropyl Ether (1) 100 g of 3-phenoxybenzyl 2-(3-chloro-4-ethoxyphenyl)-2-methylpropyl ether and 25 g of 97% potassium hydroxide were added to 300 ml of 1,3-dimethyl-2-imidazolidinone (hereinafter referred to as DMI) and the mixture was stirred at 150° C. for 18 h. After cooling to room temperature, the mixture was poured into water and made acidic with a concentrated aqueous hydrochloric acid solution. After extraction with benzene, the benzene solution was washed with water and dried. Benzene was distilled off under reduced pressure and the obtained oily residue was purified according to a column chromatography (silica gel, developer: benzene) to obtain 45.6 g of 3-phenoxybenzyl 2-3-chloro-4-hydroxyphenyl)-2-methylpropyl ether (m.p. 68° to 69° C.).

(2) 20.0 g of 3-phenoxybenzyl 2-(3-chloro-4-hydroxyphenyl)-2-methylpropyl ether prepared in the above step (1), 2.67 g of 95% sodium hydroxide and 1.0 g of 5% Pd-C (50% hydrous) were added to 100 ml of 80% methanol and the mixture was stirred at 100° C. under a hydrogen pressure of 20 to 30 kg/cm$^2$G for 6 h. After cooling, the catalyst was removed by filtration and the catalyst was washed thoroughly with benzene. The solvent wa distilled off under reduced pressure. A dilute aqueous hydrochloric acid solution was added to the distillation residue. After extraction with benzene, the benzene solution was washed with water and dried. Benzene was distilled off under reduced pressure to obtain 18.2 g of intended 3-phenoxybenzyl 2-(4-hydroxyphenyl)-2-methylpropyl ether (m.p. 69.2° to 70.0° C.).

$\delta_{TMS}^{CDCl_3}$ (ppm): 1.29(6 H,s), 3.36(2 H,s), 4.38(2 H,s), 5.07(1 H,s), 6.6–7.4(13 H,m)

Elementary Analysis for $C_{23}H_{24}O_3$

|  | C | H |
| --- | --- | --- |
| calculated (%) | 79.28 | 6.94 |
| found (%) | 79.41 | 6.87 |

REFERENTIAL EXAMPLE 2

Preparation of 1-(3-Phenoxyphenyl)-4-(4-Hydroxyphenyl)-4-Methylpentane

A mixture of 5.0 g of 1-(3-phenoxyphenyl)-4-(4-methoxyphenyl)-4-methylpentane, 30 ml of 47% hydrobromic acid and 30 ml of acetic acid was heated under reflux for 8 h. After cooling to room temperature, the reaction mixture was poured into water. After extraction with benzene, the benzene solution was washed with water and dried. Benzene was distilled off under reduced pressure and the obtained oily product was purified according to column chromatography (silica gel, developer: benzene) to obtain 4.2 g of 1-(3-phenoxyphenyl)-4-(4-hydroxyphenyl)-4-methylpentane.

$n_D^{19.4}$ 1.5870

$\nu_{max}^{neat}$(cm$^{-1}$): 3400, 1610, 1515, 1485, 1440, 1240, 1210, 825, 755, 690, 675.

$\delta_{TMS}^{CCl_4}$ (ppm): 1.00–1.68(4 H,m), 1.20(6 H,s), 2.43(2 H,t), 5.52(1 H,broad s), 6.56–7.38(13 H,m)

REFERENTIAL EXAMPLE 3

Preparation of 1-(3-Phenoxy-4-Fluorophenyl)-4-(4-Hydroxyphenyl)-4-Methylpentane

The same procedure as in Referential Example 2 was repeated except that 5.0 g of 1-(3-phenoxy-4-fluorophenyl)-4-(4-methoxyphenyl)-4-methylpentane was used to obtain 3.0 g of 1-(3-phenoxy-4-fluorophenyl)-4-(4-hydroxyphenyl)-4-methylpentane.

$n_D^{19.9}$ 1.5760

$\nu_{max}^{neat}$(cm$^{-1}$): 3360, 1620, 1600, 1520, 1435, 1285, 1220, 1130, 840, 760, 700.

$\delta_{TMS}^{CCl_4}$ (ppm): 1.02–167(4 H,m), 1.21(6 H,s), 2.39(2 H,t), 5.24(1 H,broad s), 6.52–7.35(12 H,m)

PREPARATION EXAMPLE 1

Preparation of 3-Phenoxybenzyl 2-(4-Difluorobromomethoxyphenyl)-2-Methylpropyl Ether (Compound No. 1 in Table 1)

A solution of 21.6 g of 3-phenoxybenzyl 2-(4-hydroxyphenyl)-2-methylpropyl ether and 13.9 g of potassium t-butoxide in 120 ml of DMI was added dropwise to a solution of 80 g of dibromodifluoromethane in 50 ml of DMI under stirring over 30 min while the temperature was kept at 50° to 60° C. and the mixture was kept at that temperature for additional 3 h. The mixture was poured into water and extracted with toluene. The toluene solution was washed with dilute hydrochloric acid solution and then with water and dried. Toluene was distilled off under reduced pressure to obtain 29.4 g of an oily residue. The oily residue was purified according to column chromatography [600 g of silica gel, developer: toluene/hexane (1:1)] to obtain 12.4 g of 3-phenoxybenzyl 2-(4-difluorobromomethoxyphenyl)-2-methylpropyl ether. $n_D^{20}$ 1.5545

$\nu_{max}^{neat}$(cm$^{-1}$): 1260, 1230, 1205, 1150, 1110, 1020.

$\delta_{TMS}^{CCl_4}$ (ppm): 1.33(6 H,s), 3.37(2 H,s), 4.39(2 H,s), 6.78–7.4(13 H,m)

mass spectrometric analysis (EI Mass): m/z 264, 477 (M$^+$).

PREPARATION EXAMPLE 2

Preparation of 3-Phenoxybenzyl 2-(4-Trifluoromethoxyphenyl)-2-Methylpropyl Ether (Compound No. 9 in Table 1)

1.30 g of 3-phenoxybenzyl 2-(4-difluorobromomethoxyphenyl)-2-methylpropyl ether was dissolved in 10 ml of isopropyl ether. 5 ml of hydrofluoric acid/pyridine [pyridinium poly(hydrogen fluoride)] was added to the solution and then 0.5 g of mercuric oxide was added thereto. The mixture was stirred at room temperature for 5 h and then poured into water. After extraction with hexane, the hexane solution was washed with a dilute aqueous sodium hydroxide solution and then water and dried. Hexane was distilled off under reduced pressure. 1.10 g of an oily residue thus obtained was purified according to column chromatography (40 g of silica gel, developer: toluene/hexane (2:3)) to obtain 1.05 g of intended 3-phenoxybenzyl 2-(4-trifluoromethoxyphenyl)-2-methylpropyl ether.

$n_D^{20}$ 1.5312

$\nu_{max}^{neat}$(cm$^{-1}$): 1270, 1220, 1175, 1120

$\delta_{TMS}^{CCl_4}$ (ppm): 1.31(6 H,s), 3.34(2 H,s), 4.36(2 H,s), 6.78–7.36(13 H,m)

mass spectrometric analysis (EI Mass): m/z 203, 416 (M$^+$).

PREPARATION EXAMPLE 3

Preparation of 3-Phenoxy-4-Fluorobenzyl 2-(4-Trifluoromethoxyphenyl)-2-Methylpropyl Ether (Compound No. 10 in Table 1)

(1) 4.0 g of 3-phenoxybenzyl 2-(4-trifluoromethoxyphenyl)-2-methylpropyl ether prepared in Preparation Example 2 was dissolved in 50 ml of chloroform. Then, 2.6 g of trimethylsilyl iodide was added dropwise thereto at 0° C. After completion of the addition, the mixture was stirred at room temperature for 3.5 h. 10 ml of methyl alcohol was added thereto and the reaction solution was washed with sodium hydrogensulfite, sodium hydrogencarbonate and water successively. After drying, chloroform was distilled off to obtain 6.0 g of an oily product. It was purified according to column chromatography [silica gel, developer: hexane/ethyl acetate (8:1)] to obtain 1.7 g of 2-(4-trifluoromethoxyphenyl)-2-methylpropyl alcohol.

$n_D^{20}$ 1.4540 $\nu_{max}^{neat}$(cm$^{-1}$): 3400, 1520, 1270, 1230, 1170, 1050

$\delta_{TMS}^{CCl_4}$ (ppm): 1.34(6 H,s), 1.45(1 H,s), 3.48(2 H,s), 7.17(2 H,broad d, $J_{AB}$=8.7 Hz), 7.39(2 H,d,$J_{AB}$=8.7 Hz).

mass spectrometric analysis (EI Mass): m/z 202, 216, 234 (M$^+$).

(2) 1.4 g of 2-(4-trifluoromethoxyphenyl)-2-methylpropyl alcohol prepared in the above step (1), 2.6 g of 3-phenoxy-4-fluorobenzyl bromide and 0.6 g of triethylbenzylammonium bromide were added to 20 ml of a 50% aqueous NaOH solution and the mixture was stirred at room temperature for 3 h. Water was added thereto. After extracting with benzene, the benzene solution was washed with a dilute hydrochloric acid solution and then water and dried. Benzene was distilled off under reduced pressure and 3.6 g of an oily product thus obtained was purified according to column chromatography [silica gel, developer: toluene/hexane (1:4)] to obtain 2.0 g of 3-phenoxy-4-fluorobenzyl 2-(4-trifluoromethoxyphenyl)-2-methylpropyl ether.

$n_D^{20}$ 1.5208

$\nu_{max}^{neat}$(cm$^{-1}$): 1580, 1500, 1480, 1260, 1200, 1155, 1100, 1085

$\delta_{TMS}^{CCl_4}$ (ppm): 1.31(6 H,s), 3.34(2 H,s), 4.36(2 H,s), 6.8–7.4(12 H,m)

mass spectrometric analysis (EI Mass): m/z 203, 434 (M$^+$).

PREPARATION EXAMPLE 4

Preparation of 3-Phenoxy-4-Fluorobenzyl 2-(4-Difluorobromomethoxyphenyl)-2-Methylpropyl Ether (Compound No. 2 in Table 1)

(1) 3.0 g of 3-phenoxybenzyl 2-(4-difluorobromomethoxyphenyl)-2-methylpropyl ether prepared in Preparation Example 1 was treated in the same manner as in Preparation Example 3-(1) to obtain 1.2 g of 2-(4-difluorobromomethoxyphenyl)-2-methylpropyl alcohol.

mass spectrometric analysis (EI Mass): m/z 264, 277, 295 (M$^+$).

(2) The same procedure as in Preparation Example 3-(2) was repeated except that 1.4 g of 2-(4-trifluoromethoxyphenyl)-2-methylpropyl alcohol was replaced with 1.7 g of 2-(4-difluorobromomethoxyphenyl)-2-methylpropyl alcohol to obtain 1.5 g of 3-phenoxy-4-fluorobenzyl 2-(4-difluorobromomethoxyphenyl)-2-methylpropyl ether.

$n_D^{20}$ 1.5440 mass spectrometric analysis (EI Mass): m/z 264, 495 (M$^+$).

PREPARATION EXAMPLE 5

Preparation of 1-(3-Phenoxyphenyl)-4-Difluorobromomethoxyphenyl)-4-Methylpentane (Compound No. 3 in Table 1)

20.0 g of 1-(3-phenoxyphenyl)-4-(4-hydroxyphenyl)-4-methylpentane and 13.0 g of potassium t-butoxide were dissolved in 120 ml of DMI. The solution was added dropwise to a mixture of 80 g of dibromodifluoromethane and 50 ml of DMI under stirring over 30 min while the temperature was kept at 50° to 60° C. The mixture was kept at that temperature for 3 h. The mixture was poured into water and extracted with toluene. The toluene solution was washed with dilute hydrochloric acid solution and then with water and dried. Toluene was distilled off under reduced pressure and an oily residue thus obtained was purified according to column chromatography [silica gel, developer: toluene/hexane (1:2)] to obtain 12.6 g of intended 1-(3-phenoxyphenyl)-4-(4-difluorobromomethoxyphenyl)-4-methylpentane.

$n_D^{20}$ 1.5482

$v_{max}^{neat}$(cm$^{-1}$): 1580, 1480, 1240, 1205, 1095, 1140, 1000

$\delta_{TMS}^{CCl_4}$ (ppm): 1.1–1.8(4 H,m), 1.28(6 H,s), 2.47(2 H,t,J=6.8 Hz), 6.6–7.4(13 H,m)

PREPARATION EXAMPLE 6

Preparation of 1-(3-Phenoxy-4-Fluorophenyl)-4-(4-Difluorobromomethoxyphenyl)-4-Methylpentane (Compound No. 4 in Table 1)

The same procedure as in Preparation Example 5 was repeated except that 20 g of 1-(3-phenoxyphenyl)-4-(4-hydroxyphenyl)-4-methylpentane was replaced with 20 g of 1-(3-phenoxy-4-fluorophenyl)-4-(4-hydroxyphenyl)-4-methylpentane to obtain 13.5 g of 1-(3-phenoxy-4-fluorophenyl)-4-(4-difluorobromomethoxyphenyl)-4-methylpentane.

$n_D^{20}$ 1.5480

$v_{max}^{neat}$(cm$^{-1}$): 1580, 1505, 1485, 1280, 1210, 1160, 1140, 1000

$\delta_{TMS}^{CCl_4}$ (ppm): 1.1–1.8(4 H,m), 1.30(6 H,s), 2.45(2 H,t,J=6.9 Hz), 6.6–7.4(12 H,m)

PREPARATION EXAMPLE 7

Preparation of 3-Phenoxybenzyl 2-(4-Difluorochloromethoxyphenyl)-2-Methylpropyl Ether (Compound No. 5 in Table 1)

4.3 g of 3-phenoxybenzyl 2-(4-hydroxyphenyl)-2-methylpropyl ether, 2.8 g of potassium t-butoxide and 50 ml of DMI were placed in a 200 ml autoclave. Then 10 g of difluorobromochloromethane was added thereto at room temperature and the temperature was slowly elevated to 65° C. The mixture was kept at that temperature for 3 h and then cooled to room temperature. The reaction solution was poured into water. After extraction with toluene, the toluene solution was washed with water and dried. Toluene was distilled off under reduced pressure. The oily product thus prepared was purified according to column chromatography [silica gel, developer: toluene/hexane (2:3)] to obtain 2.8 g of intended 3-phenoxybenzyl 2-(4-difluorochloromethoxyphenyl)-2-methylpropyl ether.

$\delta_{TMS}^{CCl_4}$ (ppm): 1.35(6 H,s), 3.39(2 H,s), 4.36(2 H,s), 6.75–7.45(13 H,m).

mass spectrometric analysis (EI Mass): m/z 219, 432 (M$^+$).

PREPARATION EXAMPLE 8

Preparation of 1-(3-Phenoxy-4-Fluorophenyl)-4-(4-Difluorochloromethoxyphenyl)-4-Methylpentane (Compound No. 8 in Table 1)

4.2 g of 1-(3-phenoxy-4-fluorophenyl)-4-(4-hydroxyphenyl)-4-methylpentane, 2.8 g of potassium t-butoxide and 50 ml of DMI were placed in a 200 ml autoclave. 10 g of difluorobromochloromethane was added thereto at room temperature and then the temperature was slowly elevated to 65° C. The mixture was kept at that temperature for 3 h and then cooled to room temperature.

The reaction solution was poured in water and extracted with toluene. The toluene solution was washed with water and dried. Toluene was distilled off under reduced pressure. The oily product thus prepared was purified according to column chromatography [silica gel, developer: toluene/hexane (2:3)] to obtain 1.8 g of intended 1-(3-phenoxy-4-fluorophenyl)-4-(4-difluorochloromethoxyphenyl)-4-methylpentane.

$\delta_{TMS}^{CCl_4}$ (ppm): 1.1–1.8(4 H,m), 1.24(6 H,s), 2.43(2 H,s), 6.6–7.4(12 H,m).

mass spectrometric analysis (EI Mass): m/z 219, 448 (M$^+$).

PREPARATION EXAMPLE 9

Preparation of 1-(3-Phenoxyphenyl)-4-(4-Difluorochloromethoxyphenyl)-4-Methylpentane (Compound No. 7 in Table 1)

The same procedure as in Example 8 was repeated except that 4.2 g of 1-(3-phenoxy-4-fluorophenyl)-4-(4-hydroxyphenyl)-4-methylpentane was replaced with 4.2 g of 1-(3-phenoxyphenyl)-4-(4-hydroxyphenyl)-4-methylpentane to obtain 1.6 g of 1-(3-phenoxyphenyl)-4-(4-difluorochloromethoxyphenyl)-4-methylpentane.

$\delta_{TMS}^{CCl_4}$ (ppm): 1.1–1.8(4 H,m), 1.25(6 H,s), 2.45(2 H,s), 6.6–7.4(13 H,m).

mass spectrometric analysis (EI Mass): m/z 219, 430 (M$^+$).

PREPARATION EXAMPLE 10

Preparation of 1-(3-Phenoxyphenyl)-4-(4-Trifluoromethoxyphenyl)-4-Methylpentane (Compound No. 11 in Table 1)

1.2 g of 1-(3-phenoxyphenyl)-4-(4-difluorobromomethoxyphenyl)-4-methylpentane was dissolved in 10 ml of isopropyl ether. 5 ml of hydrofluoric acid/pyridine [piridinium poly(hydrogen fluoride)] was added to the solution and then 1.0 g of mercuric oxide was added thereto. The mixture was stirred at room temperature for 3 h and then poured into water. After extraction with hexane, the hexane solution was washed with dilute aqueous sodium hydroxide solution and then with water and dried. Hexane was distilled off under reduced pressure. 1.10 g of an oil residue thus obtained was purified according to column chromatography [40 g of silica gel, developer: toluene/hexane (2:3)] to obtain 1.0 g of intended 1-(3-phenoxyphenyl)-4-(4-trifluoromethoxyphenyl)-4-methylpentane.

$n_D^{20}$ 1.5340

$v_{max}^{neat}$(cm$^{-1}$): 1265, 1220, 1170

$\delta_{TMS}^{CCl_4}$ (ppm): 1.1–1.8(4 H,m), 1.27(6 H,s), 2.48(2 H,s), 6.6–7.4(13 H,m)

mass spectrometric analysis (EI Mass): m/z 203, 414 (M$^+$).

PREPARATION EXAMPLE 11

Preparation of 1-(3-Phenoxy-4-Fluorophenyl)-4-(4-Trifluoromethoxyphenyl)-4-Methylpentane (Compound No. 12 in Table 1)

The same procedure as in Example 10 was repeated except that 1.2 g of 1-(3-phenoxyphenyl)-4-(4-difluorobromomethoxyphenyl)-4-methylpentane was replaced with 1.2 g of 1-(3-phenoxy-4-fluorophenyl)-4-(4-difluorobromomethoxyphenyl)-4-methylpentane to obtain 0.90 g of 1-(3-phenoxy-4-fluoro-phenyl)-4-(4-trifluoromethoxyphenyl)-4-methylpentane $n_D^{20}$ 1.5248 $v_{max}^{neat}$(cm$^{-1}$): 1270, 1220, 1170

$\delta_{TMS}^{CCl_4}$ (ppm): 1.0–1.7(4 H,m), 1.26(6 H,s), 2.44(2 H,s), 6.6–7.4(12 H,m)

mass spectrometric analysis (EI Mass): m/z 203, 432 (M+).

Other compounds of the general formula (XIV) shown in Table 1 can also be prepared in the same manner as above. [Insecticidal resin coating film]

EXAMPLE 1

33 parts by weight of acrylonitrile, 62 parts by weight of butyl acrylate, 3 parts by weight of hydroxyethyl methacrylate, 2 parts by weight of methacrylic acid were mixed with 0.5 parts by weight of sodium dodecylbenzene sulfonate as an emulsifier and 40 parts by weight of water by high-shere mixer to prepare a premixed monomer emulsion.

60 parts by weight of water was placed in a 2000 ml flask which the agitator was set and heated up to 70° C.

0.5 parts by weight of potassium persulfate was added into a flask and 10% of a premixed monomer emulsion was added, and polymerized for 1 hr. Then residual premixed monomer emulsion was added dropwise to a flask for 3 hrs. and the mixture was stirred furthermore for 3 hrs. at same temperature. The intended acrylic emulsion was obtained. An insecticidal component shown in Table 2 in an amount shown in Table 3, for 100 parts by weight of the resin component, was dissolved in acetone and the solution was added dropwise to the emulsion. The mixture was stirred to obtain an insecticidal resin composition in the form of an aqueous dispersion.

The insecticidal resin composition thus obtained was applied to a galvanized sheet steel by means of a bar coater so that the film thickness after drying would be about 30 to 40 μ. One groups of samples were dried at room temperature for 1 day, the others were dried at 100° C. for 10 min., the steel was cut into test pieces to be subjected to the insecticidal activity tests.

The insecticidal activity test piece was covered with a deep Petri dish having a diameter of 9 cm and a height of 9 cm. Living cockroaches were entered thereto and butter was applied to the inner surface of the Petri dish so that they could not climb up the wall but stayed on the test piece. The Petri dish was kept at 25° C. in an assay chamber for 24 h. Then the number of living cockroaches was counted to determine the death rate.

The results are shown in Tables 3 and 4.

TABLE 2

| | | |
|---|---|---|
| General formula (I) | | |
| (1) 1a | | 3-phenoxybenzyl 2-(4-ethoxyphenyl)-2-methylpropyl ether |
| (2) 1b | | 3-phenoxy-4-fluorobenzyl 2-(4-ethoxyphenyl)-2-methylpropyl ether |
| (3) 1c | | 1-(3-phenoxy-4-fluorophenyl)-4-(4-ethoxyphenyl)-4-methylpentane |
| (4) 1d | | 3-phenoxybenzyl 2-(4-chlorophenyl)-2-isopropylethyl ether |
| General formula (II) | | |
| (5) | | 3-phenoxybenzyl neopentyl ether |
| General formula (III) | | |
| (6) | | 3-phenoxybenzyl 2,2,3,3-tetramethylcyclopropylmethyl ether |
| General formula (IV) | | |
| (7) | | 3'-phenoxybenzyl 2,2-dimethyl-3-(2,2-dichlorovinyl)cyclopropanecarboxylate |
| (8) | | 3'-phenoxy-α-cyano-4'-fluorobenzyl 2,2-dimethyl-3-(2,2-dichlorovinyl)cyclopropanecarboxylate |
| (9) | | 3'-phenoxy-α-cyanobenzyl 2,2-dimethyl-3-(2,2-dichlorovinyl)cyclopropanecarboxylate |
| (10) | | 3'-phenoxy-α-cyanobenzyl 2,2-dimethyl-3-(2,2-dibromovinyl)cyclopropanecarboxylate |
| (11) | | 3'-phenoxy-α-cyanobenzyl 2,2-dimethyl-3-(1,2,2,2-tetrabromoethyl)cyclopropanecarboxylate |
| (12) | | 3'-phenoxy-α-cyanobenzyl 2,2-dimethyl-3-(2,2-dibromo-1,2-dichloroethyl)cyclopropanecarboxylate |
| (13) | | 3'-phenoxy-α-cyanobenzyl 2,2-dimethyl-3-(4-tert-butylphenyl)cyclopropanecarboxylate |
| General formula (V) | | |
| (14) | | 3'-phenoxy-α'-cyanobenzyl α-isopropyl-4-chlorophenylacetate |
| (15) | | 3'-phenoxy-α'-cyanobenzyl α-isopropyl-4-difluoromethoxyphenylacetate |
| (16) | | 3'-phenoxy-α'-cyanobenzyl 2,2-dichloro-1-(4-ethoxyphenyl)cyclopropanecarboxylate |
| (17) | | 3'-phenoxy-α'-ethynylbenzyl 1-(4-ethoxyphenyl)-2,2,3,3-tetrafluorocyclobutanecarboxylate |
| General formula (VI) | | |
| (18) | | 5'-benzyl-3'-furylmethyl-α-isopropyl (p-methoxyphenyl)acetate |
| General formula (VII) | | |
| (19) | | 3'-phenoxy-α'-cyanobenzyl α-isopropyl(2-chloro-4-trifluoromethylanilino)acetate |
| General formula (XVII) | | |
| (20) No. 1 | | 3-phenoxybenzyl 2-(4-difluorobromomethoxyphenyl)-2-methylpropyl ether |
| (21) No. 2 | | 3-phenoxy-4-fluorobenzyl 2-(4-difluorobromomethoxyphenyl)-2-methylpropyl ether |
| (22) No. 3 | | 1-(3-phenoxyphenyl)-4-(4-difluorobromomethoxyphenyl)-4-methylpentane |
| (23) No. 4 | | 1-(3-phenoxy-4-fluorophenyl)-4-(4-difluorobromomethoxyphenyl)-4-methylpentane |
| (24) No. 5 | | 3-phenoxybenzyl 2-(4-difluorochloromethoxyphenyl)-2-methylpropyl ether |
| (25) No. 9 | | 3-phenoxybenzyl 2-(4-trifluoromethoxyphenyl)-2-methylpropyl ether |
| (26) No. 11 | | 1-(3-phenoxyphenyl)-4-(4-trifluoromethoxyphenyl)-4-methylpentane. |

TABLE 3

| Amount of insecticide (parts by weight) | Death rate (drying at room temperature) | | | | | | | | | | |
|---|---|---|---|---|---|---|---|---|---|---|---|
| | 1 | 2 | 3 | 5 | 20 | 21 | 22 | 23 | 24 | 25 | 26 |
| 0.07 | 30 | 20 | 30 | 20 | 40 | 40 | 30 | 30 | 40 | 30 | 40 |
| 0.1 | 70 | 80 | 80 | 50 | 90 | 80 | 90 | 100 | 90 | 70 | 100 |
| 0.5 | 80 | 80 | 100 | 70 | 100 | 100 | 100 | 100 | 100 | 100 | 100 |
| 1.0 | 100 | 100 | 100 | 90 | 100 | 100 | 100 | 100 | 100 | 100 | 100 |
| 3.0 | 100 | 100 | 100 | 100 | 100 | 100 | 100 | 100 | 100 | 100 | 100 |
| 7.0 | 100 | 100 | 100 | 100 | 100 | 100 | 100 | 100 | 100 | 100 | 100 |
| 10.0 | 100 | 100 | 100 | 100 | 100 | 100 | 100 | 100 | 100 | 100 | 100 |

TABLE 4

| Amount of insecticide (parts by weight) | Death rate (drying at 100° C. for 10 minutes) | | | | | | | | | | |
|---|---|---|---|---|---|---|---|---|---|---|---|
| | 1 | 2 | 3 | 5 | 20 | 21 | 22 | 23 | 24 | 25 | 26 |
| 0.07 | 30 | 30 | 20 | 10 | 50 | 40 | 40 | 40 | 50 | 20 | 50 |
| 0.1 | 70 | 70 | 70 | 50 | 80 | 80 | 100 | 100 | 100 | 60 | 70 |
| 0.5 | 90 | 100 | 80 | 90 | 100 | 90 | 100 | 100 | 100 | 90 | 100 |
| 1.0 | 100 | 100 | 100 | 100 | 100 | 100 | 100 | 100 | 100 | 100 | 100 |
| 3.0 | 100 | 100 | 100 | 100 | 100 | 100 | 100 | 100 | 100 | 100 | 100 |
| 7.0 | 100 | 100 | 100 | 100 | 100 | 100 | 100 | 100 | 100 | 100 | 100 |
| 10.0 | 100 | 100 | 100 | 100 | 100 | 100 | 100 | 100 | 100 | 100 | 100 |

EXAMPLE 2

Monomers shown in Table 5 were emulsion-polymerized in an ordinary manner to prepare an acrylic resin emulsion. 3 parts by weight, for 100 parts by weight of the resin component, of an insecticidal component shown in Table 2 was dissolved in acetone and the solution was added dropwise to the emulsion to prepare an insecticidal resin composition in the form of an aqueous dispersion.

The insecticidal resin composition thus obtained was applied to a galvanized sheet steel by means of a bar coater so that the film thickness after drying would be about 30 to 40 μ. After drying at room temperature for 1 day, the steel was cut into test pieces. They were subjected to the insecticidal activity tests. When the acrylonitrile content is more than 50 wt. %, a film cannot be formed even when the insecticidal resin composition in the form of the aqueous dispersion is applied to the substrate, since the resin composition is too hard to form a film from the emulsion particles and the particles are dried as they are. For this reason, when acrylic emulsion No. 7 or No. 8 was used, 5 parts by weight, per 100 parts by weight of the resin, of 2-methyl pyrrolidone in which the acrylonitrile-containing resin was highly soluble, instead of 2 parts by weight of Texanol that was usually used as coalescence. These products were especially dried at 100° C. for 10 min. The acrylic resin emulsion No. 9 containing 75 wt. % of acrylonitrile formed no film and it became a powder. The activity of the emulsion No. 9 could thus not be examined.

The death rate was determined after 3 h and 24 h in the same manner as in Example 1 to obtain the results shown in Table 6.

TABLE 5

| Composition No. | 1 | 2 | 3 | 4 | 5 | 6 | 7 | 8 | 9 |
|---|---|---|---|---|---|---|---|---|---|
| Acrylonitrile | 0 | 3 | 5 | 15 | 30 | 40 | 50 | 65 | 75 |
| Methyl methacrylate | 33 | 30 | 28 | 18 | 3 | | | | |
| Butyl acrylate | 62 | 62 | 62 | 62 | 62 | 55 | | | |
| 2-Ethylhexyl acrylate | | | | | | | 45 | 30 | 20 |
| Hydroxyethyl methacrylate | 3 | 3 | 3 | 3 | 3 | 3 | 3 | 3 | 3 |
| Methacrylic acid | 2 | 2 | 2 | 2 | 2 | 2 | 2 | 2 | 2 |
| Texanol* | 2 | 2 | 2 | 2 | 2 | 2 | | | |
| 2-Methylpyrrolidone | | | | | | | 5 | 5 | 5 |

*Trade name of a product of Eastman Chemical Co. (solvent mainly comprising 2,2,4-trimethyl-1,3-pentanediol monoisobutyrate)

TABLE 6

| AN content (wt. %) | (1) | | (2) | | (3) | | (4) | | (5) | | (6) | | (7) | | (8) | | (9) | |
|---|---|---|---|---|---|---|---|---|---|---|---|---|---|---|---|---|---|---|
| | 3 h | 24 h | 3 h | 24 h | 3 h | 24 h | 3 h | 24 h | 3 h | 24 h | 3 h | 24 h | 3 h | 24 h | 3 h | 24 h | 3 h | 24 h |
| 0 | 0 | 0 | 0 | 20 | 0 | 20 | 0 | 0 | 0 | 0 | 0 | 0 | 0 | 10 | 0 | 30 | 0 | 10 |
| 3 | 0 | 20 | 0 | 30 | 0 | 50 | 0 | 20 | 0 | 10 | 0 | 20 | 0 | 30 | 30 | 60 | 0 | 30 |
| 5 | 30 | 60 | 30 | 80 | 40 | 90 | 0 | 60 | 0 | 30 | 20 | 30 | 30 | 50 | 40 | 70 | 50 | 60 |
| 15 | 50 | 80 | 50 | 100 | 70 | 100 | 40 | 70 | 30 | 70 | 50 | 80 | 60 | 90 | 70 | 100 | 50 | 100 |
| 30 | 80 | 100 | 80 | 100 | 90 | 100 | 40 | 80 | 50 | 100 | 50 | 90 | 60 | 90 | 70 | 100 | 90 | 100 |
| 40 | 80 | 100 | 100 | 100 | 100 | 100 | 60 | 70 | 60 | 90 | 90 | 100 | 60 | 100 | 70 | 100 | 90 | 100 |
| 50 | 100 | 100 | 100 | 100 | 100 | 100 | 80 | 90 | 100 | 100 | 90 | 100 | 90 | 100 | 90 | 100 | 100 | 100 |
| 65 | 100 | 100 | 100 | 100 | 100 | 100 | 90 | 100 | 90 | 100 | 100 | 100 | 80 | 90 | 100 | 100 | 100 | 100 |

| AN content (wt. %) | (10) | | (11) | | (12) | | (13) | | (14) | | (15) | | (16) | | (17) | | (18) | |
|---|---|---|---|---|---|---|---|---|---|---|---|---|---|---|---|---|---|---|
| | 3 h | 24 h | 3 h | 24 h | 3 h | 24 h | 3 h | 24 h | 3 h | 24 h | 3 h | 24 h | 3 h | 24 h | 3 h | 24 h | 3 h | 24 h |
| 0 | 0 | 20 | 0 | 0 | 0 | 0 | 0 | 0 | 0 | 0 | 0 | 0 | 0 | 10 | 0 | 20 | 0 | 0 |
| 3 | 0 | 30 | 0 | 40 | 0 | 30 | 0 | 20 | 20 | 30 | 0 | 20 | 0 | 10 | 0 | 10 | 0 | 10 |
| 5 | 40 | 60 | 30 | 60 | 40 | 50 | 10 | 40 | 50 | 90 | 30 | 60 | 40 | 40 | 30 | 30 | 30 | 50 |
| 15 | 80 | 100 | 30 | 90 | 50 | 80 | 30 | 70 | 60 | 90 | 50 | 90 | 50 | 80 | 60 | 80 | 60 | 90 |
| 30 | 100 | 100 | 60 | 90 | 70 | 90 | 50 | 90 | 80 | 100 | 80 | 100 | 70 | 100 | 80 | 90 | 70 | 100 |
| 40 | 100 | 100 | 80 | 100 | 70 | 100 | 60 | 90 | 100 | 100 | 90 | 100 | 80 | 100 | 90 | 100 | 90 | 100 |
| 50 | 100 | 100 | 100 | 100 | 100 | 100 | 70 | 100 | 100 | 100 | 100 | 100 | 100 | 100 | 100 | 100 | 100 | 100 |
| 65 | 100 | 100 | 100 | 100 | 100 | 100 | 90 | 100 | 100 | 100 | 100 | 100 | 100 | 100 | 100 | 100 | 100 | 100 |

| AN content (wt. %) | (19) | | (20) | | (21) | | (22) | | (23) | | (24) | | (25) | | (26) | |
|---|---|---|---|---|---|---|---|---|---|---|---|---|---|---|---|---|
| | 3 h | 24 h | 3 h | 24 h | 3 h | 24 h | 3 h | 24 h | 3 h | 24 h | 3 h | 24 h | 3 h | 24 h | 3 h | 24 h |
| 0 | 0 | 0 | 0 | 30 | 0 | 30 | 0 | 0 | 0 | 10 | 0 | 10 | 0 | 30 | 0 | 20 |
| 3 | 0 | 20 | 20 | 20 | 10 | 50 | 0 | 30 | 20 | 50 | 0 | 50 | 0 | 60 | 0 | 40 |
| 5 | 40 | 60 | 40 | 80 | 40 | 90 | 30 | 70 | 40 | 100 | 20 | 80 | 30 | 90 | 30 | 80 |
| 15 | 70 | 90 | 70 | 100 | 80 | 100 | 70 | 100 | 100 | 100 | 70 | 100 | 80 | 100 | 70 | 100 |
| 30 | 80 | 100 | 100 | 100 | 100 | 100 | 100 | 100 | 90 | 100 | 100 | 100 | 100 | 100 | 90 | 100 |
| 40 | 90 | 100 | 100 | 100 | 100 | 100 | 100 | 100 | 100 | 100 | 100 | 100 | 100 | 100 | 100 | 100 |
| 50 | 100 | 100 | 100 | 100 | 100 | 100 | 100 | 100 | 100 | 100 | 100 | 100 | 100 | 100 | 100 | 100 |
| 65 | 100 | 100 | 100 | 100 | 100 | 100 | 100 | 100 | 100 | 100 | 100 | 100 | 100 | 100 | 100 | 100 |

EXAMPLE 3

30 wt. %, based on the resin, of acrylonitrile, 65 wt. % of butyl acrylate, 2 wt. % of methacrylic acid and 3 wt. % of hydroxyethyl methacrylate were solution-polymerized in methyl ethyl ketone solvent to obtain an acrylic resin solution. 1, 3 or 7 parts by weight, for 100 parts by weight of the resin, of 3-phenoxybenzyl 2-(4-ethoxyphenyl)-2-methylpropyl ether was dissolved in acetone. This solution was added dropwise to the acrylic resin solution to prepare an insecticidal resin solution. The insecticidal resin solution was applied to a galvanized steel sheet so that the film thickness after drying would be about 30 to 40 μ. After drying at room temperature, the sheet was cut into pieces to be subjected to the insecticidal activity tests.

The insecticidal activity tests were conducted in the same manner as in Example 1 to obtain the results shown in Table 7.

TABLE 7

| Amount of insecticide (parts by weight) | Death rate After 3 h | After 24 h |
|---|---|---|
| 1 | 0 | 80 |
| 3 | 10 | 100 |
| 7 | 40 | 100 |

What is claimed is:

1. An insecticidal resin coating film, which comprises; 100 parts by weight of a copolymer resin or acrylonitrile and/or methacrylonitrile and another monomer; and 0.1 to 10 parts by weight of an insecticide selected from the group consisting of the following general formulae (II), (III), (XIII) and (XIV):

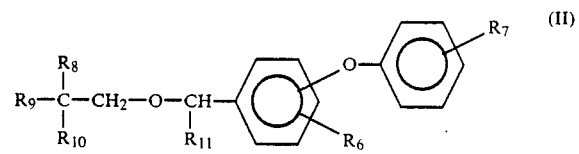

wherein $R_8$, $R_9$ and $R_{10}$ each represent a hydrogen or halogen atom or an alkyl group of 1 to 6 carbon atoms, $R_{11}$ represents a hydrogen atom or a cyano or ethynyl group and $R_6$ and $R_7$ are $R_6$ represents a hydrogen or halogen atom and $R_7$ represents $R_6$ or alkoxy of 1 to 4 carbon atoms;

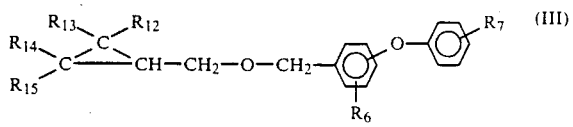

wherein $R_{12}$, $R_{13}$, $R_{14}$ and $R_{15}$ each represent a hydrogen or halogen atom or an alkyl or alkenyl group each having 1 to 6 carbon atoms, and $R_6$ and $R_7$ are as defined above;

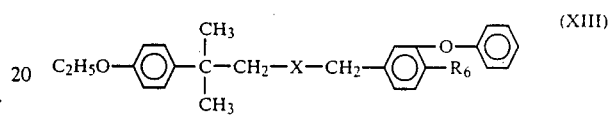

wherein X represents an oxygen atom or methylene group and $R_6$ represents a hydrogen or fluorine atom; and

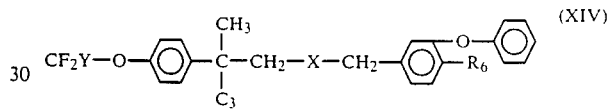

wherein Y represents a hydrogen, chlorine, bromine or fluorine atom, X represents an oxygen atom or methylene group and $R_6$ represents a hydrogen or fluorine atom.

2. An insecticidal resin coating film according to claim 1 wherein the amount of acrylonitrile or methacrylonitrile in the copolymer resin is 5 to 65 wt. %.

3. An insecticidal resin coating film according to claim 1 wherein the amount of acrylonitrile and/or methacrylonitrile in the copolymer resin is 15 to 50 wt. %.

* * * * *